United States Patent
Giannini et al.

[11] Patent Number: 5,147,310
[45] Date of Patent: Sep. 15, 1992

[54] PRESSURE INFUSION SYSTEM

[76] Inventors: Peter T. Giannini, 1891 River Valley Dr., Germantown, Tenn. 38138; Dennis H. Currie, 2982 Mt. Terrace, Memphis, Tenn. 38127

[21] Appl. No.: 753,920

[22] Filed: Sep. 3, 1991

Related U.S. Application Data

[63] Continuation-in-part of Ser. No. 612,602, Nov. 13, 1990, abandoned.

[51] Int. Cl.⁵ .............................................. A61M 5/14
[52] U.S. Cl. ............................ 604/141; 128/DIG. 12
[58] Field of Search ................. 604/141, 142, 152; 128/DIG. 12

[56] References Cited

U.S. PATENT DOCUMENTS

| | | | |
|---|---|---|---|
| 4,430,078 | 2/1984 | Sprague | 604/141 |
| 4,539,005 | 9/1985 | Greenbelt | 604/141 |
| 4,626,244 | 12/1986 | Reinicke | 604/141 |
| 4,955,860 | 9/1990 | Ruano | 604/141 |

*Primary Examiner*—Paul J. Hirsch
*Attorney, Agent, or Firm*—Walker, McKenzie & Walker

[57] ABSTRACT

A valve for a pressure infusion system. The valve includes a body having a first port for being coupled to a source of pressurized fluid, a second port for being coupled to a bladder of the pressure infusion system, a third port for being vented to the atmosphere, and an open interior for connecting the second and third ports to one another and for allowing pressurized fluid to pass therebetween. Each of the second and third ports has a cross sectional area greater than the cross sectional area of the first port to allow pressurized fluid to quickly escape from the interior of the bladder through the second and third ports. A plug is positioned within the body for movement between an inflate position and a deflate position. The first and second ports are open and the third port is blocked when the plug is in the inflate position for allowing inflation of the bladder. The first port is blocked and the second and third ports are opened when the plug is in the deflate position for allowing rapid deflation of the bladder.

24 Claims, 5 Drawing Sheets

FIG. 17

PRESSURE INFUSION SYSTEM

CROSS-REFERENCE TO RELATED APPLICATION

This is a continuation-in-part of my pending application, Ser. No. 07/612,602, filed Nov. 13, 1990, now abandoned entitled "Improvement Pressure Infusion System".

BACKGROUND OF THE INVENTION

1. Field of the Invention

The present invention relates, in general, to pressure infusion systems for allowing fluid to be infused into a patient.

2. Information Disclosure Statement

A preliminary patentability search conducted in class 604, subclasses 118, 141, 142 and 147, and class 222, subclass 96 produced the following patents which may relate to the present invention, copies of which were submitted with the parent application:

Price, U.S. Pat. No. 2,362,025. Price discloses an apparatus for administering blood plasma that includes a bulb for being manually and intermittently compressed to force blood plasma from the apparatus into a patient's vein.

Beall et al., U.S. Pat. No. 3,153,414. Beall et al. discloses an infusion system that includes an inflatable bladder for being wrapped about a flexible liquid container and a hand inflation bulb for manually inflating the bladder to force liquid from the liquid container.

Ilg, U.S. Pat. Nos. 3,328,255 and 3,399,040 and Re. 27,132. Ilg discloses an elongated bag for freezing and washing blood cells. The bag has a pair of opposed outer flexible and collapsible walls and an intermediate wall dividing the bag into a gas chamber and a liquid chamber sealed from each other. By introducing gas into the gas chamber, its volume is increased and the volume of the liquid chamber is decreased whereby the level of stratified liquid in the liquid chamber is forced upwardly without disturbing the strata until the upper spent wash strata flows out of an outlet at the top of the liquid chamber.

Bierman, U.S. Pat. No. 3,468,308. Bierman discloses a pressure infusion device that expels liquid from a bladder member at an extremely slow rate over an extended period. The device includes a flexible bladder and a rigid outer shell surrounding the bladder. Means is provided to admit pressurized gas into the outer shell at a slow and controlled rate to force liquid from the bladder member.

Cogley et al., U.S. Pat. No. 3,838,794. Cogley et al. discloses a package for storing and dispensing liquids. The package includes a fluid-tight outer vessel and a flexible fluid-tight container within the outer vessel. A port is provided for allowing pressurized fluid to be introduced into the interior of the outer vessel.

Hinck et al., U.S. Pat. No. 4,090,514. Hinck et al. discloses a pressure infusion device which includes a bladder as part of the cuff in which a fluid filled bag is encased wherein the bladder surrounds at least eighty per cent of the fluid filled bag. A flexible bag is coupled to the bladder for allowing the bladder to be manually inflated.

Leibinsohn, U.S. Pat. No. 4,507,116. Leibinsohn discloses an apparatus for the induced infusion of a liquid from a flexible liquid bag. The Leibinsohn apparatus includes a bulb and an accumulator for accumulating pressurized fluid pumped by the bulb to maintain substantially constant pressure as liquid is forced from the liquid bag.

Marx, U.S. Pat. No. 4,573,992. Marx discloses an apparatus for receiving and reinfusing a patient's own blood. The apparatus includes a rigid outer container and a readily deformable inner container located within the rigid outer container. Blood is drawn into the inner container by suction and is displaced therefrom by pressurized gas being introduced between the outer and inner containers.

Woods et al., U.S. Pat. No. 4,657,160. Woods et al. discloses a pressure infusion system including a flexible bag containing a quantity of liquid to be infused, a pressure cuff for causing the liquid to be forced from the bag, and a control assembly for controlling the pressure cuff. The control assembly includes a manually operative valve for allowing pressurized gas to inflate the pressure cuff to force liquid from the bag, and for allowing a vacuum to be applied to the pressure cuff to quickly deflate the pressure cuff.

Keime, U.S. Pat. No. 4,673,392. Keime discloses a portable, self-contained injector for perfusions. The injector includes a fluidtight casing enclosing a flexible bag containing fluid to be injected. A compression assembly including a pressurized gas cartridge is provided for pressurizing the interior of the casing to force fluid from the flexible bag.

Bellin et al., U.S. Pat. No. 4,735,613. Bellin et al. discloses a pressure infusion device having a pressure gauge fastened directly in the pressure applying bag which presses against a sealed bag of liquid to be infused.

Additionally, during the prosecution of the parent application the following references were cited by the Examiner:

Sprague, U.S. Pat. No. 4,430,078; Greenblatt, U.S. Pat. No. 4,539,005; Reinicke, U.S. Pat. No. 4,626,244; and Ruano, U.S. Pat. No. 4,955,860.

None of the above patents disclose or suggest the present invention. More specifically, none of the above patents disclose or suggest a pressure infusion system having a valve means including, in general, body means having first port means for being coupled to a source of pressurized fluid and for being in communication with the interior of a bladder of a pressure infusion cuff, second port means for being coupled to said bladder and for being in communication with the interior of said bladder, third port means for being vented to the atmosphere, and an open interior for connecting the second and third port means to one another and for allowing pressurized fluid to pass therebetween; each of the second and third port means having a cross sectional area greater than the cross sectional area of the first port means to allow pressurized fluid to quickly escape from the interior of the bladder through the second and third port means; and plug means positioned within the body means for movement between an inflate position and a deflate position; the first and second port means being open and the third port means being blocked when the plug means is in the inflate position for allowing inflation of the bladder of the pressure infusion cuff; the first port means being blocked and the second and third port means being opened when the plug means is in the deflate position for allowing rapid deflation of the bladder of the pressure infusion cuff.

SUMMARY OF THE INVENTION

The present invention is directed toward providing an improved pressure infusion system. The concept of the present invention is to provide a pressure infusion system with a unique valve means which allows a pressure infusion bag to be replaced in less than 20 seconds.

The valve means of the present invention includes, in general, body means having first port means for being coupled to a source of pressurized fluid and for being in communication with a bladder of a pressure infusion cuff, second port means for being coupled to said interior of said bladder for being in communication with the interior of said bladder, third port means for being vented to the atmosphere, and an open interior for connecting the second and third port means to one another and for allowing pressurized fluid to pass therebetween; each of the second and third port means having a cross sectional area greater than the cross sectional area of the first port means to allow pressurized fluid to quickly escape from the interior of the bladder through the second and third port means; and plug means positioned within said body means for movement between an inflate position and a deflate position; the first and second port means being open and the third port means being blocked when the plug means is in the inflate position for allowing inflation of the bladder of the pressure infusion cuff; the first port means being blocked and the second and third port means being opened when the plug means is in the deflate position for allowing rapid deflation of the bladder of the pressure infusion cuff.

DESCRIPTION OF THE PREFERRED EMBODIMENTS

Figure 1:
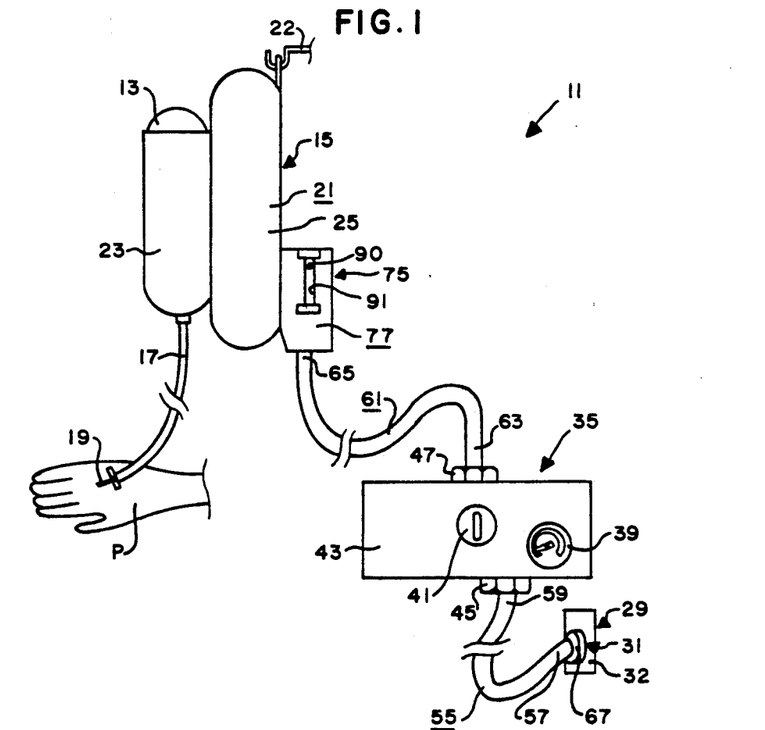
FIG. 1 is a somewhat diagrammatic view of a first embodiment of the improved pressure infusion system of the present invention shown in operation.
Figure 2:
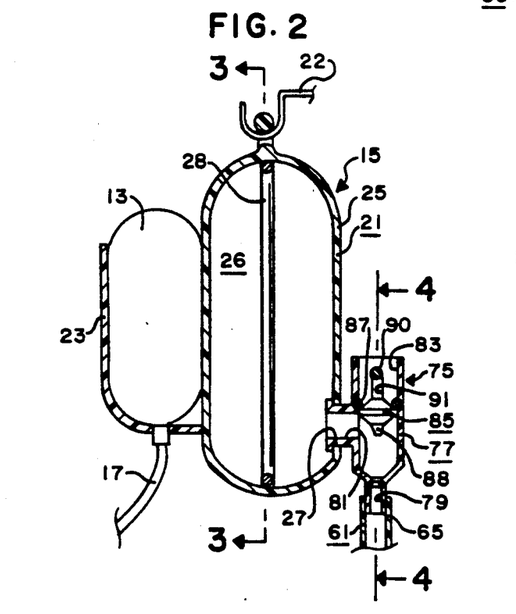
FIG. 2 is an enlarged sectional view of a portion of FIG. 1.
Figure 3:
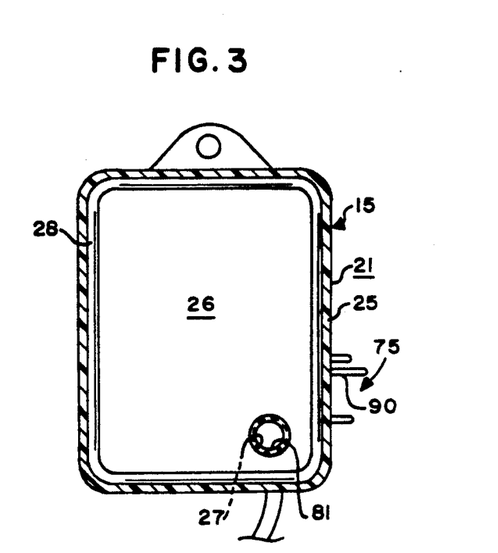
FIG. 3 is a sectional view substantially as taken on line 3—3 of FIG. 2 with portions thereof omitted for clarity.
Figure 4:
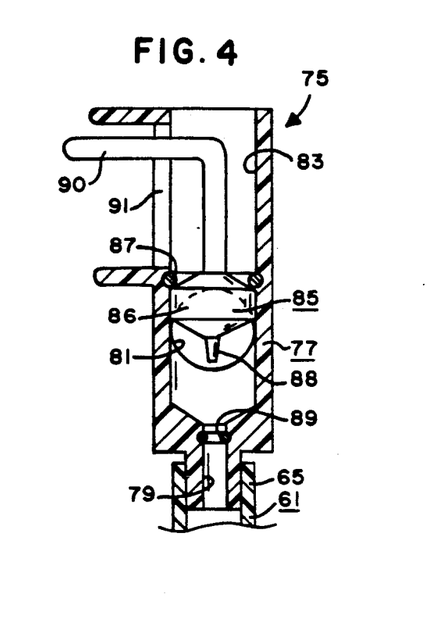
FIG. 4 is an enlarged sectional view substantially as taken on line 4—4 of FIG. 2 with portions thereof omitted for clarity.
Figure 5:
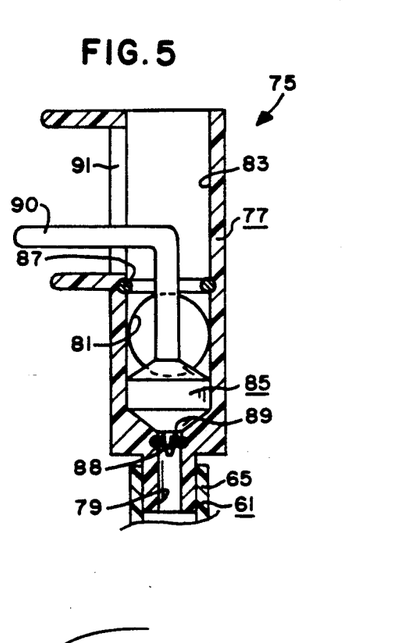
FIG. 5 is a sectional view similar to FIG. 4 but with portions thereof in a moved position.
Figure 6:
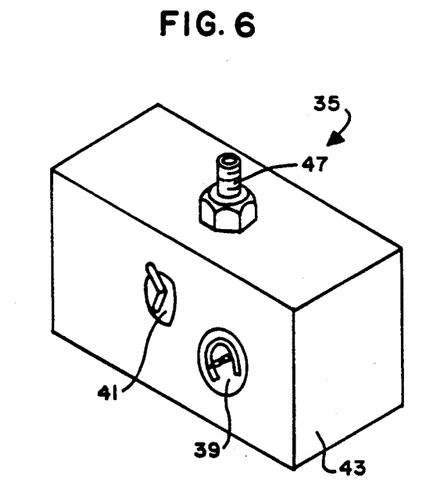
FIG. 6 is a perspective view of a portion of FIG. 1.
Figures 8, 9, 10:
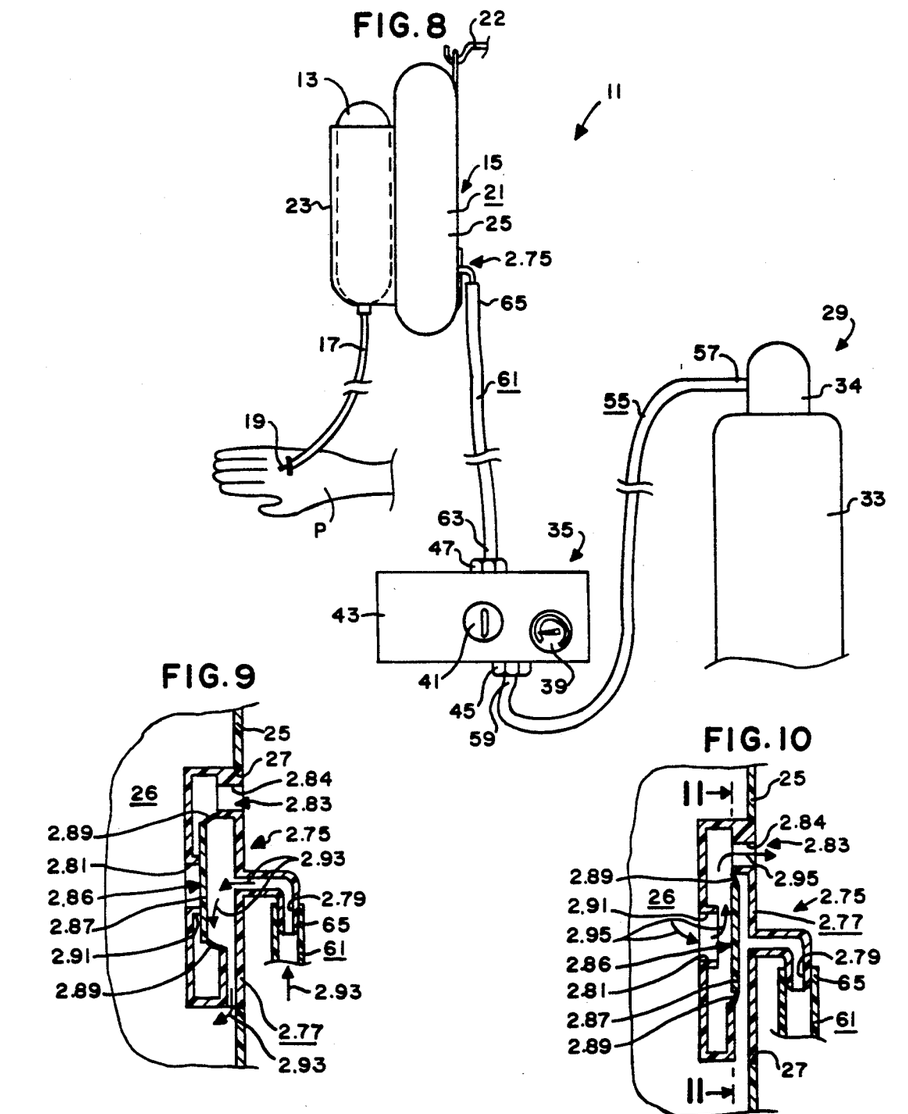
FIG. 8 is a somewhat diagrammatical view of a second embodiment of the improved pressure infusion system of the present invention shown in operation.
FIG. 9 is an enlarged sectional view of a portion of FIG. 8.
FIG. 10 is a sectional view similar to FIG. 9 but with portions thereof in a moved position.
Figure 11:
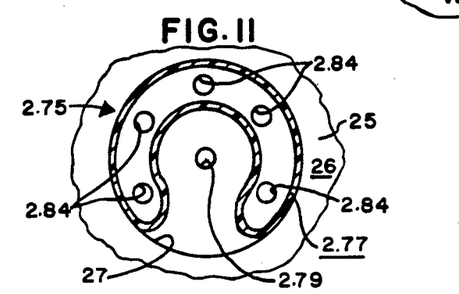
FIG. 11 is a sectional view substantially as taken on line 11—11 of FIG. 10.
Figure 12:
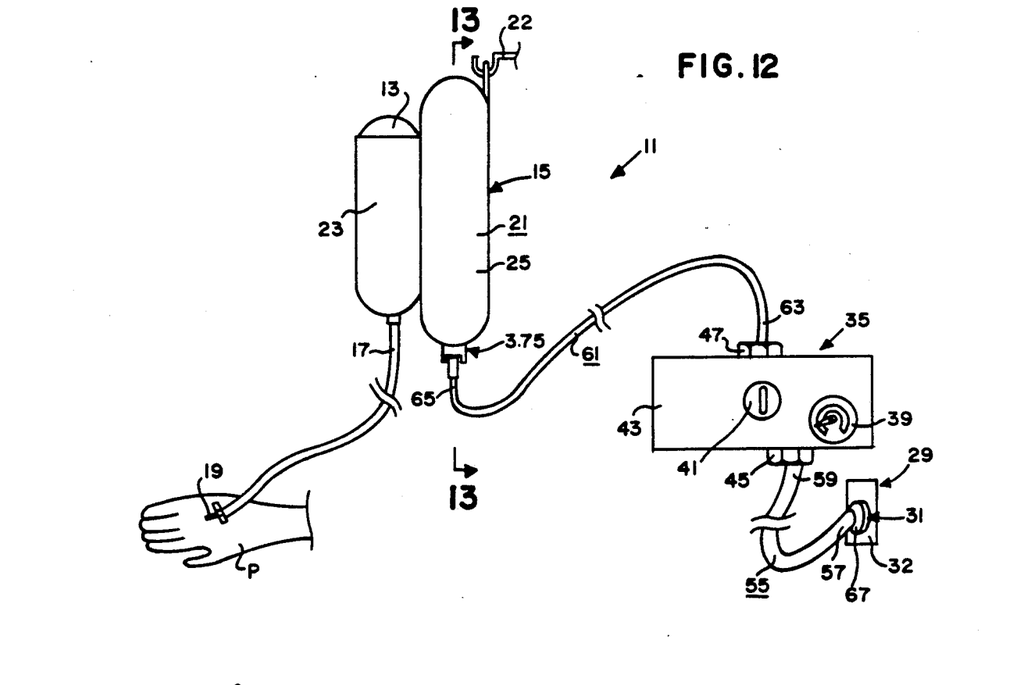
FIG. 12 is a somewhat diagrammatical view of a third embodiment of the improved pressure infusion system of the present invention shown in operation.
Figure 13:
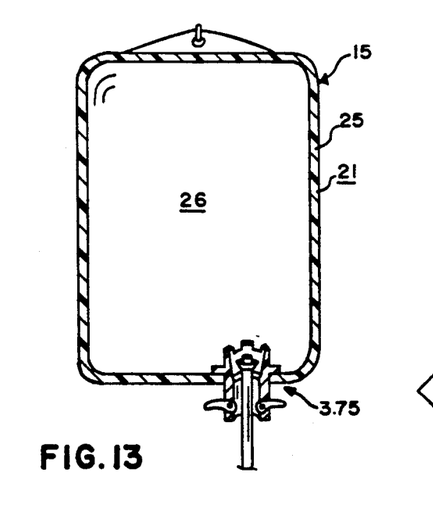
FIG. 13 is a sectional view substantially as taken on line 13—13 of FIG. 12 with portions thereof omitted for clarity.
Figure 14:
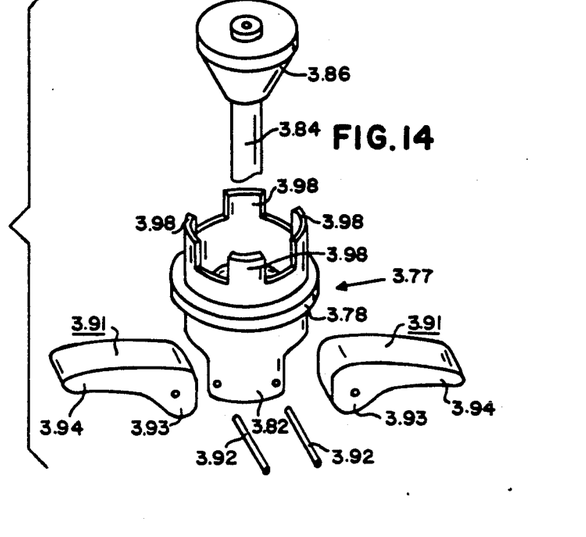
FIG. 14 is an exploded view of certain of the components of the third embodiment of the present invention

An improved pressure infusion system for infusing liquid into a patient P is shown, in general, in FIGS. 1, 8 and 12 identified by the numeral 11. The pressure infusion system 11 includes a flexible bag 13 for containing a quantity of liquid to be infused and a pressure means 15 for selectively applying pressure to the bag 13 to force liquid from the bag 13.

The bag 13 preferably consists of a conventional liquid filled, flexible plastic bag which can contain various infusible fluids, such as blood, necessary for a patient P during surgical or emergency procedures. A tube 17 extends from the bag 13 to a needle 19 for being inserted into the body of the patient P as will now be apparent to those skilled in the art. The specific construction of the bag 13, tube 17, and needle 19 may vary as will now be apparent to those skilled in the art. However, the bag 13, tube 17, and needle 19 are preferably commercially available, off-the-shelf type units and the specific construction thereof forms no part of this invention.

The pressure means 15 preferably includes a pressure infusion cuff 21 holding the bag 13 and for being hung from the hook 22 of a standard IV-pole or the like. The cuff 21 has a bag-like pocket 23 for receiving the bag 13 and has an inflatable bladder 25 for movement between a deflated position in which the bag 13 can be easily inserted into or removed from the pocket 23 and an inflated position in which pressure will be applied to the bag 13 in such a manner that fluid will be forced therefrom The bladder 25 has a hollow interior 26 and is preferably air-tight except for a port 27 provided therein for allowing pressurized fluid to pass into the interior 26 of the bladder 25 to inflate the bladder 25 and to exit the interior 26 of the bladder 25 to deflate the bladder 25 in a manner which will hereinafter be described. Urging means such as a wire 28 is preferably provided within the interior 26 of the bladder 25 to expedite deflation of the bladder 25 by urging the bladder 25 to the deflated position. The specific construction of the cuff 21 may vary as will now be apparent to those skilled in the art.

When the bladder 25 is inflated in a manner hereinafter to be described, pressure is applied to the bag 13 to force the liquid out of the bag 13, through the tube 17 and needle 19, and into the patient P. When the bladder 25 is subsequently deflated in a manner hereinafter to be described, pressure is removed from the bag 13 to allow the bag 13 to be easily removed from the pocket 23. The time required to deflate the bladder 25, remove the bag 13 from the pocket 23, insert a new bag 13 into the pocket 23, and reinflate the bladder 25 can be of critical importance during surgical or emergency procedures. The present invention includes valve means having an inflate position for allowing inflation of the bladder 25 of the infusion cuff 21 and having a deflate position for allowing rapid deflation of the bladder 25 of the infusion cuff 21. The valve means is preferably attached to and integral with the bladder 25 in a manner which will hereinafter be described The system 11 includes a source 29 of pressurized fluid for supplying pressurized fluid to the bladder 25 through the valve means to inflate the bladder 25 and force liquid from the bag 13. The term "pressurized fluid" as used herein includes pressurized air, pressurized gas, and the like. The source 29 of pressurized fluid may include the standard pressurized gas outlet port 31 commonly mounted on a panel 32 or the like provided on the wall of a typical hospital room or the like (see FIGS. 1 and 12) to supply pressurized oxygen and the like to a patient, etc., as will now be apparent to those skilled in the art. Such pressurized gas outlet port typically supplies gas at approximately 50 psig (pounds per square inch gauge), positive pressure However, the source 29 of pressurized fluid may include a tank 33 of pressurized gas or the like (see FIG. 8) rather than the standard pressurized gas outlet port 31, as will now be apparent to those skilled in the art. Since such tanks 33 typically provide pressurized fluid at a much greater pressure than the hospital wall-supplied pressurized gas, a regulator 34 is preferably used in combination with such a tank 33 to reduce the pressure of the gas passing therefrom to approximately 50 psig.

Figure 7:
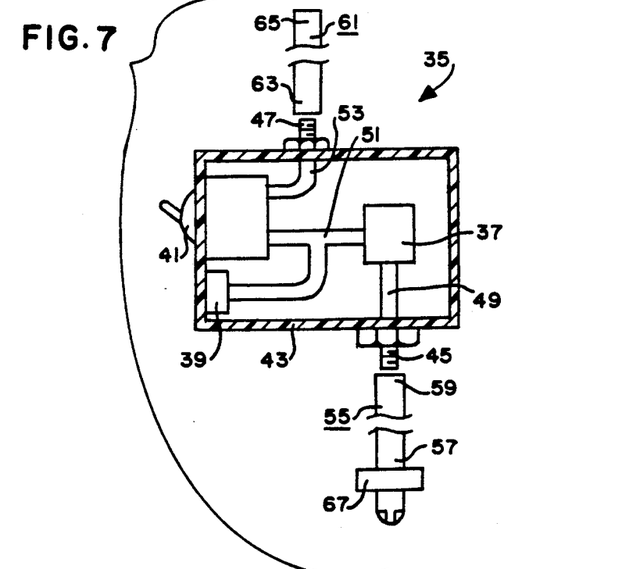
FIG. 7 is an exploded sectional view of a portion of FIG. 1.

The system 11 preferably includes control means 35 positioned between the source 29 of pressurized fluid and the valve means for controlling the passage of pressurized fluid from the source 29 of pressurized fluid to the valve means. The control means 35 preferably includes regulator means 37 for reducing the pressure of the pressurized fluid passing from the source 29 of pressurized fluid to the valve means to about 5.8 psig, positive pressure. The regulator valve 37 may be a conventional regulator valve of typical construction and operation now apparent to those skilled in the art. The control means 35 preferably includes a pressure gauge 39 for providing an indication of the pressure of the pressurized fluid leaving the regulator valve 37. The pressure gauge 39 may be a conventional dial-type pressure gauge of typical construction and operation for providing a visual indication of the pressure of the pressurized fluid leaving the regulator valve 37 as will now be apparent to those skilled in the art. The control means 35 preferably includes an on off switch means 41 for allowing the passage of pressurized fluid between the source 29 of pressurized fluid and the valve means to be easily and completely opened and closed. The on-off switch means 41 may be a conventional lever-type on-off pneumatic valve of typical construction and operation as will now be apparent to those skilled in the art. The control means 35 preferably includes a box-like housing 43 to which the regulator valve 37, pressure gauge 39, and on-off switch means 41 are mounted. The housing 43 has an inlet port 45 and an outlet port 47. The control means 35 includes a first conduit 49 connecting the inlet port 45 to the regulator valve 37, a second conduit 5 connecting the regulator valve 37 to the pressure gauge 39 and the on-off switch means 41, and a third conduit 53 connecting the on-off switch means 41 to the outlet port 47 as clearly shown in FIG. 7. The second conduit 51 includes a conventional Tee for communicating with all three elements as will now be apparent to those skilled in the art.

The system 11 includes a first conduit 55 having a first end 57 for being coupled to the source 29 of pressurized fluid (e.g., to the pressurized gas outlet port 31) and having a second end 59 for being coupled to the inlet port 45 of the housing 43 of the control means 35 to allow pressurized fluid to pass from the source 29 of pressurized gas to the control means 35. The system 11 also includes a second conduit 61 having a first end 63 for being coupled to the outlet port 47 of the housing 43 of the control means 35 and having a second end 65 for being coupled to the valve means to allow pressurized fluid to pass from the control means 35 to the valve means. The conduits 55, 61 are preferably constructed from elongated lengths of flexible hose or the like typically used in hospitals and the like to transfer pressurized fluid such as oxygen from such pressurized gas outlet ports, etc., as will now be apparent to those skilled in the art. Such hoses typically have a one-fourth inch (approximately 6.35 millimeters) inside diameter A typical plug-in type connector 67 is preferably attached to the first end 57 of the first conduit 55 to allow easy connection to the pressurized gas outlet port 31 in a manner as will now be apparent to those skilled in the art.

A first embodiment of the valve means of the present invention is shown in FIGS. 1-5 and identified by the numeral 75. The valve means 75 includes a body means 77 for being attached to the pressure means 15. More specifically, the body means 77 is preferably fixedly attached to the bladder 25. The body means 77 has a first or inlet port means 79 for being coupled to the source 29 of pressurized fluid (i.e., for being coupled to the second end 65 of the second conduit 61), a second port means 81 for being coupled to the bladder 25 in communication with the port 27, a third or vent port means 83 for being vented to the atmosphere, and an opened interior for connecting the first, second and third port means 79, 81, 83 to one another and for allowing pressurized fluid to pass therebetween (see, in general, FIG. 2). A critical feature of the present invention is to make the cross sectional area of the second port means 81 and the cross sectional area of the third port means 83 greater than the cross sectional area of the first port means 79 to thereby allow pressurized fluid to quickly escape from the interior 26 of the bladder 25 when the valve means 75 is moved to the deflate position. More specifically, the first port means 79 preferably has a ⅛ inch internal diameter, the second port means 81 preferably has an internal diameter greater than ⅛ inch and less than 1 inch (e.g., ½ inch), and the third port means 83 preferably has an internal diameter greater than ⅛ inch and less than 1 inch (e.g., ½ inch). The body means 77 may be constructed in various manners and out of various materials as will now be apparent to those skilled in the art. Thus, for example, the body means 77 may be molded out of plastic o the like.

The valve means 75 preferably has plug means 85 positioned within the open interior of the body means 77. The plug means 85 preferably includes a body member 86 movable between an inflate position (see FIG. 4) in which pressurized fluid is allowed to pass from the second conduit 61, through the first port means 79, through a portion of the open interior of the body means 77, through the second port means 81, and through the port 27 into the bladder 25 to inflate the bladder 25 and force fluid from the bag 13. The plug means 85 has a deflate position (see FIG. 5) in which pressurized fluid is allowed to pass from the bladder 25, through the port 27, through the second port means 81, through a portion of the open interior of the body means 77, and out the third port means 83 into the atmosphere to allow the bladder 25 to rapidly deflate. When in the inflate position, the body member 86 completely blocks the third port means 83 from the first and second port means 79, 81 to prevent the pressurized fluid from passing from the open interior of the body means 77 through the third port means 83 into the atmosphere. The valve means 75 preferably includes a first O-ring 87 adjacent the third port means 83 for coacting with the body member 86 of the plug means 85 to create a fluid-tight blockage of the third port means 83 when the body member 86 is in the inflate position. When in the deflate position, the body member 86 completely blocks the first port means 79 to prevent pressurized fluid from entering the open interior of the body means 77 through the first port means 79. The plug means 85 may include a projection 88 for extending into the first port means 79 (see FIG. 5). The valve means 75 preferably includes a second O-ring 89 adjacent the first port means 79 for coacting with the body member 86 of the plug means 85 to create a fluid-tight blockage of the first port means 79 when the body member 86 is in the deflate position. The plug means 85 preferably includes a lever or handle 90 attached to the body member 86 for allowing the body member 86 to be easily manually moved between the inflate and deflate positions. More specifically, the handle 90 preferably extends from the body member 86 to a point outside the body means 77 through a slot 91 in the body means 77 so that a user of the system 11 can merely slide the handle 90 from one end of the slot 91 to the other end to thereby move the body member 86 between the inflate and deflate positions. The handle 90 is preferably located adjacent the pressure infusion cuff 21 for allowing manual control of the valve means 75 from a location adjacent the pressure infusion cuff 21. Thus, with the handle 90 located adjacent or on the pressure infusion cuff 21, the user of the system 11 need only reach to the pressure infusion cuff 21 to first move the handle 90 to rapidly deflate the bladder 25 and then after a few seconds remove the empty bag 13 from the pocket 23. The plug means 85 may be constructed in various manners and out of various materials as will now be apparent to those skilled in the art. Thus, for example, the plug means 85 may be molded out of plastic or the like. The O-rings 87, 89 may consist of typical rubber O-rings well known to those skilled in the art.

The operation of the system 11 with the valve means 75 is quite simple. With the plug means 85 in the deflate position, the source 29 of pressurized fluid (e.g., the pressurized gas outlet port 31 or the tank 33) is coupled to the inlet port 45 of the control means 35 via the first conduit 55. The outlet port 47 of the control means 35 is coupled to the first port means 79 of the valve means 75 via the second conduit 61. The on-off switch means 41 of the control means 35 is moved to the on-position to convey pressurized fluid to the first port means 79 of the valve means 75. The infusion cuff 21 is hung on the hook 22 and a filled bag 13 is inserted into the pocket 23. The needle 19 is inserted into the patient P and connected to the bag 13 via the tube 17. The plug means 85 is then moved to the inflate position via the lever 90, causing the bladder 25 to inflate and force fluid from the bag 13 into the patient When all of the fluid is forced out the bag 13, the plug means 85 is moved to the deflate position, causing the bladder 25 to quickly deflate. The empty bag 13 is then disconnected from the needle 19 and removed from the pocket 23. A full bag 13 is then inserted into the pocket 23 and connected to the needle 19. The plug means 85 is then moved back to the inflate position to repeat the cycle. The second port means 81 thus acts as both an inlet port for allowing pressurized fluid to pass from the interior of the body means 77 into the interior 26 of the bladder 25 when the plug means 85 is in the inflate position, and as an outlet port for allowing pressurized fluid to pass from the interior 26 of the bladder 25 to the interior of the body means 77 when the plug means 85 is in the deflate position A second embodiment of the valve means of the present invention is shown in FIGS. 8-11 and identified by the numeral 2.75. The valve means 2.75 includes a body means 2.77 for being attached to the pressure means 15. More specifically, the body means 2.77 is preferably fixedly attached to the bladder 25. The body means 2.77 has a first or inlet port means 2.79 coupled to the bladder 25 in communication with the port 27 for being coupled to the source 29 of pressurized fluid (i.e., for being coupled to the second end 65 of the second conduit 61) to allow pressurized fluid to pass into the bladder 25 from the source 29 of pressurized fluid to inflate the bladder 25, a second or outlet port means 2.81 coupled to the bladder 25 in communication with the port 27 for allowing pressurized fluid to exit the bladder 25, a third port means or vent port means 2.83 for being vented to the atmosphere, and an opened interior for connecting the inlet and outlet port means 2.79, 2.81, and the vent port means 2.83 to one another and for allowing pressurized fluid to pass therebetween (see, in general, FIGS. 9 and 10). The vent port means 2.83 preferably includes a plurality of vent ports 2.84. A critical feature of the present invention is to make the cross sectional area of the outlet port means 2.81 and the cross sectional area of the vent port means 2.83 greater than the cross sectional area of the inlet port means 2.79 to thereby allow pressurized fluid to quickly escape from the bladder 25 when the valve means 2.75 is moved to the deflate position. More specifically, the inlet port means 2.79 preferably has a ⅛ inch internal diameter, the outlet port means 2.81 preferably has an internal diameter greater than ⅛ inch and less than 1 inch (e.g., ½ inch), and the plurality of vent ports 2.84 preferably have a combined cross sectional area equal to an effective internal diameter greater than 1/8 inch and less than 1 inch (e.g., ½ inch). The body means 2.77 may be constructed in various manners and out of various materials as will now be apparent to those skilled in the art. Thus, for example, the body means 2.77 may be molded out of plastic or the like.

The valve means 2.75 preferably includes plug means positioned within the open interior of the body means 2.77. The plug means has an inflate position (see FIG. 9) in which pressurized fluid is allowed to pass from the second conduit 61, through the inlet port means 2.79, through a portion of the open interior of the body means 2.77, through the port 27, and into the bladder 25 to inflate the bladder 25 and force fluid from the bag 13. The plug means has a deflate position (see FIG. 10) in which pressurized fluid is allowed to pass from the bladder 25, through the port 27, through the outlet port means 2.81, through a portion of the open interior of the body means 2.77, and out the vent ports 2.84 into the atmosphere to allow the bladder 25 to deflate. When in the inflate position, the plug means completely blocks the outlet port means 2.81 to prevent the pressurized fluid from passing from the open interior of the body means 2.77 through the vent ports 2.84 into the atmosphere The plug means preferably includes diaphragm means 2.86 for blocking the vent port means 2.83 anytime pressurized fluid is coupled to the inlet port means 2.79 (i.e., anytime pressurized fluid is passing through the second conduit 61 to the inlet port means 2.79) and for opening the vent port means 2.83 anytime pressurized fluid is not coupled to the inlet port means 2.79 (i.e., anytime pressurized fluid is not passing through the second conduit 61 to the inlet port means 2.79 such as when the on-off switch means 41 is in the off position). The diaphragm means 2.86 preferably includes a disk member 2 87 and a flexible connecting member 2.89 for connecting the disk member 2.87 to the body means 2.77. The body means 2.77 preferably includes a seat member 2.91 about the outlet port means 2.81 for forming a fluid-tight seal with the disk member 2.87 when the plug means is in the inflate position. The movement of the plug means between the inflate and deflate positions is controlled by the passage of pressurized fluid to the valve means 2.75. More specifically, anytime pressurized fluid is passing to the inlet port means 2.79 as indicated by the arrows 2.93 in FIG. 9, the disk member 2.87 will be forced by the pressure of the pressurized fluid to the inflate position against the seat member 2.91. However, anytime the bladder 25 is inflated and the flow of pressurized fluid to the inlet port means 2.79 is subsequently stopped by, for example, moving the on-off switch means 41 of the control means 35 to the off position, the pressure of the fluid within the bladder 25 will force the disk member 2.87 to the deflate position as indicated by the arrows 2.95 in FIG. 10.

The operation of the system 11 with the valve means 2.75 is quite simple. The source 29 of pressurized fluid (e.g., the pressurized gas outlet port 31 or the tank 33) is coupled to the inlet port 45 of the control means 35 via the first conduit 55. With the on-off switch means 41 of the control means 35 in the off-position, the outlet port 47 of the control means 35 is coupled to the inlet port means 2.79 of the valve means 2.75 via the second conduit 61. The infusion cuff 21 is hung on the hook 22 and a filled bag 13 is inserted into the pocket 23. The needle 19 is inserted into the patient P and connected to the bag 13 via the tube 17. The on-off switch means 41 of the control means 35 is then moved to the on-position to convey pressurized fluid to the inlet port means 2.79 of the valve means 2.75 and force the plug means to the inflate position, causing the bladder 25 to inflate and force fluid from the bag 13 into the patient. When all of the fluid is forced out of the bag 13, the on off switch means 41 of the control means 35 is moved to the off-position, allowing the pressurized fluid within the bladder 25 to move the plug means to the deflate position and allowing the bladder 25 to quickly deflate. The empty bag 13 is then disconnected from the needle 19 and removed from the pocket 23. A full bag 13 is then inserted into the pocket 23 and connected to the needle 11. The on-off switch means 41 is then moved back to the on-position to repeat the cycle.

A third embodiment of the valve means of the present invention is shown in FIGS. 12-17 and identified by the numeral 3.75. The valve means 3.75 includes a body means 3.77 for being attached to the pressure means 15. More specifically, the body means 3.77 is preferably fixedly and sealingly attached to the bladder 25 as by extending the main part of body means 3.77 through port 27 and attaching the flange 3.78 of the body means to bladder 25 by adhesives or the like. The body means 3.77 has a first or inlet port means 3.79 coupled to the bladder 25 in communication with the port 27 and the interior 26 of bladder 25 for being coupled to the source 29 of pressurized fluid (i.e., for being coupled to the second end 65 of the second conduit 61) to allow pressurized fluid to pass into the bladder 25 from the source 29 of pressurized fluid to inflate the bladder 25, a second or outlet port means 3.81 coupled to the bladder 25 in communication with the port 27 and the interior 26 of bladder 25 for allowing pressurized fluid to exit the bladder 25, a third or vent port means 3.83 for being vented to the atmosphere, and an open interior 3.80 for connecting the outlet port means 3.81 and the vent port means 3.83 to one another and for allowing pressurized fluid to pass therebetween (see, in general, FIGS. 15, 16 and 17).

Body means 3.77 is preferably bifurcated at the lower end thereof to provide a pair of depending and spaced apart leg portions 3.82.

A critical feature of the present invention is to make the cross sectional area of the outlet port means 3.81 and the cross sectional area of the vent port means 3.83 greater than the cross sectional area of the inlet port means 3.79 to thereby allow pressurized fluid to quickly escape from the bladder 25 when the valve means 3.75 is moved to the deflate position. More specifically, the inlet port means 3.79 preferably has a $\frac{1}{8}$ inch internal diameter, the outlet port means 3.81 preferably has an internal diameter greater than $\frac{1}{8}$ inch and less than 1 inch (e.g., $\frac{1}{2}$ inch), and the vent port means 3.83 has an internal diameter greater than $\frac{1}{8}$ inch and less than 1 inch (e.g., $\frac{1}{2}$ inch). The body means 3.77 may be constructed in various manners and out of various materials as will now be apparent to those skilled in the art. Thus, for example, the body means 3.77 may be molded or machined out of plastic or the like.

The valve means 3.75 preferably includes plug means 3.85 positioned within the interior of the body means 3.77. The plug means 3.85 has an inflate position (see FIG. 15) in which pressurized fluid is allowed to pass from the second conduit 61 (see FIG. 12), through the inlet port means 3.79, through a resilient and flexible conduit 3.84 and into the interior 26 of bladder 25 to inflate the bladder 25 and force fluid from the bag 13. The plug means 3.85 has a deflate position (see FIG. 17) in which pressurized fluid is allowed to pass from the interior 26 of bladder 25, through the outlet port means 3.81, through a portion of the open interior 3.80 of the body means 3.77, and out the vent port 3.83 into the atmosphere to allow the bladder 25 to deflate. When in the inflate position, the plug means 3.85 completely blocks the outlet port means 3.81 to prevent the pressurized fluid from passing from the interior 26 of the bladder 25, through the interior of body means 2.77 and through the vent port 3.83 into the atmosphere.

Figure 15:
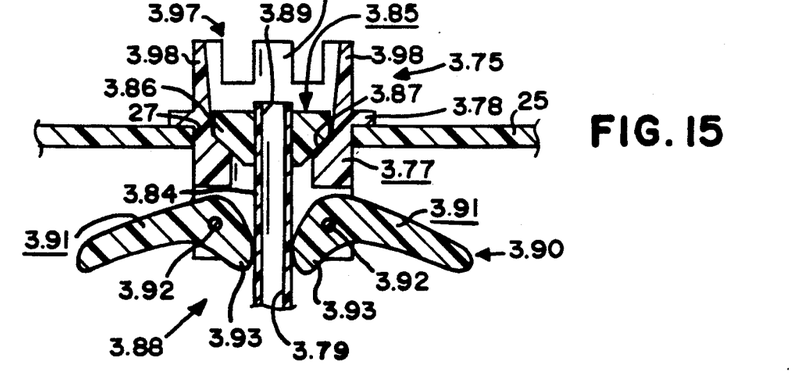
FIG. 15 is a sectional view of the valve means of the third embodiment of the present invention with the parts thereof shown in an inflate position.
Figure 16:
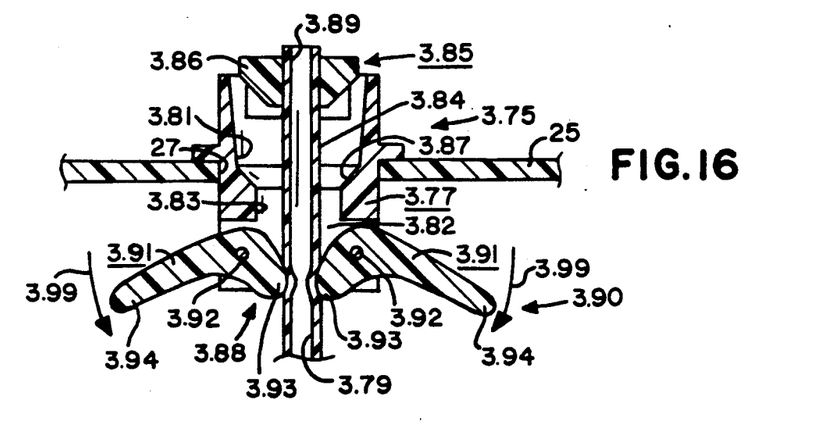
FIG. 16 is a view similar to FIG. 15 but showing the parts in an intermediate position
Figure 17:
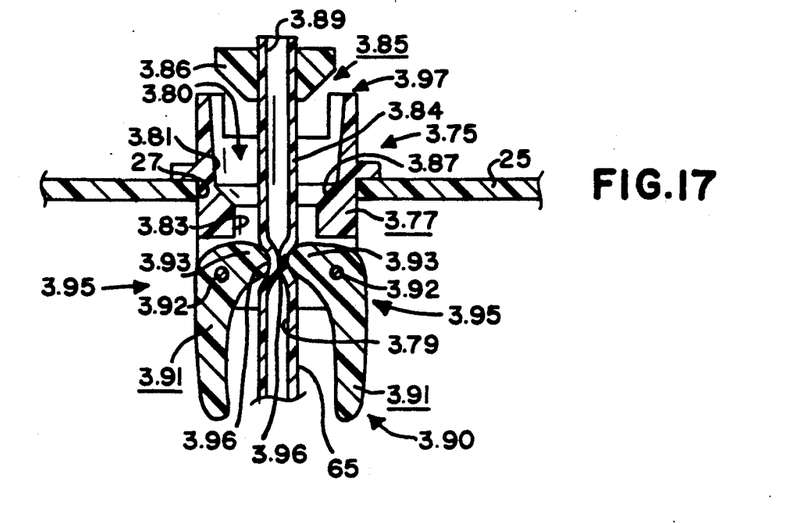
FIG. 17 is a view similar to FIG. 15 but showing the parts in a deflate position.

Plug means 3.85 includes, in general, a body member 3.86 for being moved between said inflate position, shown in FIG. 15, wherein body member 3.86 acts as a valve seating on valve seat 3.87 to block off outlet port means 3.81 and vent port means 3.83, and a deflate position, shown in FIG. 17, wherein body member 3.86 unseats from valve seat 3.87 to open up outlet port means 3.81 and vent port means 3.83. It should be understood that the movement of plug means 3.85 is shown exaggerated in FIGS. 16 and 17 for illustration purposes. Plug means 3.85 additionally includes pincher valve means 3.88 for forming a fluid-tight blockage or substantially fluid-tight blockage of inlet port means 3.79 when plug means 3.85 is in said deflate position and for moving body member 3.86 to said deflate position shown in FIG. 17 when plug means 3.85 is moved from said inflate to said deflate position.

Pincher valve means 3.88 includes flexible and resilient conduit 3.84 in communication at one end with inlet port means 3.79 and in communication at the other end thereof with the interior 26 of bladder 25. Flexible conduit 3.84 is preferably an extension of conduit 61, that is, flexible conduit 3.84 is formed from the same piece of conduit as conduit 61 and which extends beyond inlet port 3.79 to the open end 3.89 of conduit 3.84. Body member 3.86 is fixedly mounted on conduit 3.84 adjacent open end 3.89 by suitable means well known to those skilled in the art. More specifically, the end 3.89 of conduit 3.84 extends through a central aperture in body member 3.86 and is preferably held therein by suitable means as by friction between body member 3.86 and end 3.89 of conduit 3.84, or an adhesive or the like.

In addition, pincher valve means 3.88 includes lever means 3.90 movable between a first or pinching position, as seen in FIG. 17, for pinching flexible conduit 3.84 to provide fluid tight blockage of inlet port means 3.79 or to provide substantially fluid tight blockage of inlet port means 3.79 when plug means 3.85 is in said deflate position and a second or released position, as seen in FIG. 15, for releasing or substantially releasing from pinching flexible conduit 3.84 when plug means 3.85 is in said inflate position.

Body member 3.86 is responsive to movement of lever means 3.90 from said released position to said pinching position to move body member 3.86 to said deflate position and open outlet port means 3.81 and vent port means 3.83 to communicate with one another. Flexible conduit 3.84 is manually moveable downwardly by pulling downwardly on conduit 61 for moving body member 3.86 to said inflate position and at the same time moving lever means 3.90 to said released position.

Lever means 3.90 includes one and preferably a pair of levers 3.91 pivotally mounted from leg portions 3.82 on opposite sides of body means 3.77 by suitable means as pins 3.92. Each of levers 3.91 includes a nose portion 3.93 for contacting flexible conduit 3.84 and an integrally formed handle portion 3.94 for being contacted and moved manually. In addition, each of levers 3.91 includes over-center retaining means 3.95 for selectively retaining lever means 3.90 in said pinching position, as seen in FIG. 17.

The relationship of levers 3.91, pins 3.92, and flexible conduit 3.84 are preferably as follows: Pins 3.92 are preferably spaced apart along an imaginary line which is horizontal, and therefore perpendicular to the longitudinal vertical axis of flexible conduit 3.84. The pressure points 3.96 of the nose portions 3.93 on flexible conduit 3.84 when lever means 3.90 is in said pinching position are at a level which is above the pins 3.92 so that the resiliency of flexible conduit 3.84 causes outward forces to be respectively exerted on the nose portions 3.93 of levers 3.91 which retains lever means 3.90 in said pinching position and prevents levers 3.91 from accidentally moving towards said released position of lever means 3.90 shown in FIG. 15.

The friction between nose portions 3.93 and flexible conduit 3.84 should be such that when conduit 61 is manually pulled downwardly with lever means 3.90 being in said pinching position shown in FIG. 17, levers 3.91 will be caused to rotate from the positions shown in FIG. 17 (pinching position of each of the levers) to the positions shown in FIG. 15 (released position of each of the levers). It will be understood that in moving between said pinching and released positions lever mean 3.90 and levers 3.91 will move through an intermediate position shown in FIG. 16, and again, that the movement of body member 3.86 is shown exaggerated in FIGS. 16 and 17 for purposes of illustration.

Body means 3.77 may additionally include guide means 3.97 for centering body member 3.86 when the body member is being moved from said deflate position to said inflate position. Guide means 3.97 preferably includes upstanding spaced fingers 3.98 at the upper part of body means 3.77. The inner surfaces of fingers 3.98 are preferably downwardly and inwardly tapered to center the body member 3.86 on valve seat 3.87.

The operation of the system 11 with the valve means 3.75 is quite simple. The source 29 of pressurized fluid (e.g., the pressurized gas outlet port 31 or the tank 33) is coupled to the inlet port 45 of the control means 35 via the first conduit 55. With the on-off switch means 41 of the control means 35 in the off-position and the valve means 3.75 in the deflate position, the outlet port 47 of the control means 35 is coupled to the inlet port means 3.79 of the valve means 3.75 via the second conduit 61. The infusion cuff 21 is hung on the hook 22 and a filled bag 13 is inserted into the pocket 23. The needle 19 is inserted into the patient P and connected to the bag 13 via the tube 17. The on-off switch means 41 of the control means 35 is then moved to the on-position to convey pressurized fluid to the inlet port means 3.79 of the valve means 3.75. The conduit 61 is manually pulled downwardly to move plug means 3.85 to said inflate position causing the bladder 25 to inflate and force fluid from the bag 13 into the patient. When all of the fluid is forced out of the bag 13, handles 3.94 of levers 3.91 are simultaneously manually moved downwardly as shown by arrows 3.99 to said deflate position allowing the bladder 25 to quickly deflate, at which point switch means 41 may be moved to the off-position. The empty bag 13 is then disconnected from the needle 19 and removed from the pocket 23. A full bag 13 is then inserted into the pocket 23 and connected to the needle 11. The on off switch means 41 is then moved back to the on-position to repeat the cycle.

Although the present invention has been described and illustrated with respect to preferred embodiments and a preferred use therefor, it is not to be so limited since modifications and changes can be made therein which are within the full intended scope of the invention.

We claim:

1. Valve means for a pressure infusion system of the type including a flexible bag for containing a quantity of liquid for being infused into a patient, a source of pressurized fluid, and pressure means for being coupled to said bag and to said source of pressurized fluid and for selectively applying pressure to said bag to force said liquid from said bag, said pressure means including a pressure infusion cuff for holding said bag, said pressure means including an inflatable bladder for movement between a deflated position in which said bag can be easily removed from or inserted into said pressure infusion cuff and an inflated position in which pressure is applied to said bag to force liquid from said bag, said bladder having a hollow interior and having a port for allowing fluid to pass into and out of said interior of said bladder; said valve means comprising:

a) body means having first port means for being coupled to said source of pressurized fluid, second port means for being coupled to said bladder in communication with said port of said bladder, third port means for being vented to the atmosphere, and an open interior for connecting said first, second and third port means to one another and for allowing pressurized fluid to pass therebetween; each of said second and third port means having a cross sectional area greater than the cross sectional area of said first port means to allow pressurized fluid to quickly escape from said interior of said bladder through said second and third port means; and b) plug means positioned within said open interior of said body means for movement between an inflate position and a deflate position; said first and second port means being open and said third port means being blocked when said plug means is in said inflate position for allowing inflation of said bladder of said pressure infusion cuff; said first port means being blocked and said second and third port means being opened when said plug means is in said deflate position for allowing rapid deflation of said bladder of said pressure infusion cuff.

2. The valve means of claim 1 in which said plug means includes a body member for being manually slid between said inflate position and said deflate position.

3. The valve means of claim 2 in which said plug means includes a handle member attached to said body member thereof for allowing manual movement of said body member between said inflate position and said deflate position.

4. The valve means of claim 3 in which said handle member is located adjacent said pressure infusion cuff for allowing manual control of said valve means from a location adjacent said pressure infusion cuff.

5. The valve means of claim 2 in which said valve means includes a first O-ring member for coacting with said body member of said plug means to form a fluid-tight blockage of said third port means when said plug means is in said inflate position.

6. The valve means of claim 5 in which said valve means includes a second O-ring member for coacting with said body member of said plug means to form a fluid-tight blockage of said first port means when said plug means is in said deflate position.

7. The valve means of claim 1 in which said plug means includes diaphragm means for blocking said third port means anytime pressurized fluid is coupled to said first port means and for opening said third port means anytime pressurized fluid is not coupled to said first port means and said bladder is pressurized.

8. The valve means of claim 7 in which said diaphragm means includes a disk member for selectively blocking said third port means and includes a flexible connecting member for connecting said disk member to said body means.

9. The valve means of claim 8 in which said third port means includes a plurality of vent ports.

10. The valve means of claim 9 in which the combined cross sectional area of said vent ports is greater than the cross sectional area of said first port means.

11. The valve means of claim 1 in which is included urging means for expediting deflation of said bladder.

12. The valve means of claim 11 in which said urging means includes a wire provided within said interior of said bladder for urging said bladder to said deflated position.

13. The combination with a pressure infusion system including a flexible bag for containing a quantity of liquid for being infused into a patient, a source of pressurized fluid, and pressure means for being coupled to said bag and to said source of pressurized fluid and for selectively applying pressure to said bag to force said liquid from said bag, said pressure means including a pressure infusion cuff for holding said bag, said pressure means including an inflatable bladder for movement between a deflated position in which said bag can be easily removed from or inserted into said pressure infusion cuff and an inflated position in which pressure is applied to said bag to force liquid from said bag, said bladder having a hollow interior and having a port for allowing fluid to pass into and out of said interior of said bladder and a valve means for allowing inflation and rapid deflation of said bladder; said valve means comprising:

a) body means having first port means coupled to said source of pressurized fluid, second port means coupled to said bladder in communication with said port of said bladder, third port means vented to the atmosphere, and an open interior for connecting said first, second and third port means to one another and for allowing pressurized fluid to pass therebetween; each of said second and third port means having a cross sectional area greater than the cross sectional area of said first port means to allow pressurized fluid to quickly escape from said interior of said bladder through said second and third port means; and b) plug means positioned within said open interior of said body means for movement between an inflate position and a deflate position, said plug means blocking said third port means when in said inflate position; said first and second port means being open and said third port means being blocked when said plug means is in said inflate position for allowing inflation of said bladder of said pressure infusion cuff; said first port means being blocked and said second and third port means being opened when said plug means is in said deflate position for allowing rapid deflation of said bladder of said pressure infusion cuff.

14. The combination of claim 13 in which is included urging means for expediting deflation of said bladder.

15. The combination of claim 14 in which said urging means includes a wire provided within said interior of said bladder for urging said bladder to said deflated position 16. An improved pressure infusion system of the type including a flexible bag for containing a quantity of liquid for being infused into a patient, and pressure means for being coupled to a source of pressurized fluid and for selectively applying pressure to said bag to force said liquid from said bag, said pressure means including a pressure infusion cuff for holding said bag, said pressure means including an inflatable bladder for movement between a deflated position in which said bag can be easily removed from or inserted into said pressure infusion cuff and an inflated position in which pressure is applied to said bag to force liquid from said bag, said bladder having a hollow interior and having a port for allowing fluid to pass into and out of said interior of said bladder; wherein the improvement comprises valve means having an inflate position for allowing rapid inflation of said bladder of said pressure infusion cuff and having a deflate position for allowing rapid deflation of said bladder of said pressure infusion cuff, said valve means comprising:

a) body means having a first port for being coupled to said source of pressurized fluid, a second port for being coupled to said bladder in communication with said port of said bladder, a third port for being vented to the atmosphere, and an open interior for connecting said first, second and third ports to one another and for allowing pressurized fluid to pass therebetween; each of said second and third ports having a cross sectional area greater than the cross sectional area of said first port to allow pressurized fluid to quickly escape from said interior of said bladder through said second and third ports; and b) plug means positioned within said open interior of said body means for movement between an inflate position and a deflate position, said plug means blocking said third port when in said inflate position, said plug means blocking said first port when in said deflate position 17. The improved pressure infusion system of claim 16 in which is included urging means for expediting deflation of said bladder 18. The improved pressure infusion system of claim 17 in which said urging means includes a wire provided within said interior of said bladder for urging said bladder to said deflated position.

19. Valve means for a pressure infusion system of the type including a flexible bag for containing a quantity of liquid for being infused into a patient, a source of pressurized fluid, and pressure means for being coupled to said bag and to said source of pressurized fluid and for selectively applying pressure to said bag to force said liquid from said bag, said pressure means including a pressure infusion cuff for holding said bag, said pressure means including an inflatable bladder for movement between a deflated position in which said bag can be easily removed from or inserted into said pressure infusion cuff and an inflated position in which pressure is applied to said bag to force liquid from said bag, said bladder having a hollow interior and having a port for allowing fluid to pass into and out of said interior of said bladder; said valve means comprising:

a) body means having first port means for being coupled to said source of pressurized fluid and for being in communication with said interior of said bladder, second port means for being coupled to said bladder in communication with said interior of said bladder, third port means for being vented to the atmosphere, and an open interior for connecting said second and third port means to one another and for allowing pressurized fluid to pass therebetween; each of said second and third port means having a cross sectional area greater than the cross sectional area of said first port means to allow pressurized fluid to quickly escape from said interior of said bladder through said second and third port means; and b) plug means positioned within said body means for movement between an inflate position and a deflate position; said first port means being open and said third port means being blocked when said plug means is in said inflate position for allowing inflation of said bladder of said pressure infusion cuff; said first port means being blocked and said second and third port means being opened when said plug means is in said deflate position for allowing rapid deflation of said bladder of said pressure infusion cuff.

20. The valve means of claim 19 in which said plug means includes a body member for being moved between said inflate position wherein said body member blocks off said third port means and said deflate position wherein said body member opens said third port means, and in which said plug means includes pincher valve means for forming a substantially fluid-tight blockage of said first port means when said plug means is in said deflate position and for moving said body member to said deflate position when said plug means is moved from said inflate to said deflate position.

21. The valve means of claim 20 in which said pincher valve means includes a flexible conduit in communication at one end with said first port means and in communication at the other end thereof with said interior of said bladder, said body member being fixedly mounted on said flexible conduit, said pincher valve means additionally including lever means movable between a pinching position for pinching said flexible conduit to provide said substantially fluid tight blockage of said first port means when said plug means is in said deflate position and a released position for releasing from pinching said flexible conduit when said plug means is in said inflate position, said body member being responsive to movement of said lever means from said released position to said pinching position to move said body member to said deflate position and open said third port means, said flexible conduit being manually moveable downwardly for moving said body member to said inflate position and at the same time moving said lever means to said released position.

22. The valve means of claim 21 wherein said lever means includes a pair of levers pivotally mounted on said body means, each of said levers including retaining means for selectively retaining said lever means in said pinching position.

23. The valve means of claim 22 in which each of said levers includes a nose portion for contacting said flexible conduit and a handle portion for being contacted and moved manually.

24. The valve means of claim 23 in which said body means includes guide means for centering said body member when being moved from said deflate position to said inflate position.

* * * * *